United States Patent [19]
Scott et al.

[11] Patent Number: 5,994,349
[45] Date of Patent: Nov. 30, 1999

[54] 3-CARBOALKOXY-2, 3-DIHYDRO-1H-PHENOTHIAZIN-4[10H]-ONE DERIVATIVES

[75] Inventors: Kenneth R. Scott, Silver Spring, Md.; Mia L. Laws, Wilmington, Del.; Ralph R. Roberts, Cottage Grove, Minn.; Jesse M. Nicholson, Upper Marlboro, Md.

[73] Assignee: Howard University, Washington, D.C.

[21] Appl. No.: 08/958,320

[22] Filed: Oct. 27, 1997

[51] Int. Cl.$^6$ .................................................. A61K 31/54
[52] U.S. Cl. .................................. 514/224.8; 514/226.2; 544/35
[58] Field of Search .......................... 544/35; 514/224.8, 514/226.2

[56] References Cited

U.S. PATENT DOCUMENTS

| | | | |
|---|---|---|---|
| 4,636,497 | 1/1987 | Niemers et al. | 514/215 |
| 5,580,894 | 12/1996 | Scott et al. | 514/380 |

FOREIGN PATENT DOCUMENTS

| | | |
|---|---|---|
| 3229122 A1 | 9/1984 | Germany . |
| 3426564 A1 | 1/1986 | Germany . |

OTHER PUBLICATIONS

Jain et al., Chemical Abstracts, vol. 100, abstract 120987, 1984.

"Anticonvulsant Enaminones: With Emphasis on Methyl 4–[(p–Chlorophenyl)Amino]–6–Methyl–2–Oxocyclohex-3–En–1–Oate (ADD 196022)"; I.O. Edafiogho, M.S. Alexander, J.A. Moore, V.A. Farrar and K.R. Scott; Current Medicinal Chemistry, 1994, 1, 159–175.

"Synthesis and anticonvulsant activity of enaminones. 3. Investigations on 4'–, 3'–, and 2–substituted . . . "; Scott, K.R. et al.; Journal of Medicinal Chemistry, Sep. 29, 1995, 38(20) pp. 4033–4043.

"Synthesis and anticonvulsant activity of enaminones. 2. Further Structure–activity correlations."; Scott, K.R., Edafiogho, I.O., Richardson E.L., J.A. et al.; Journal of Medicinal Chemistry, Jul. 9, 1993, 36(14) pp. 1947–1955.

"Synthesis and anticonvulsant activity of enaminones."; Edafiogho, I.O., Hinko, C.N., Chang, H., Moore, J.A. et al.; Journal of Medicinal Chemistry, Jul. 24, 1992, 35(15) pp. 2798–2805.

"Nuclear magnetic resonance studies of anticonvulsant enaminones."; Edafiogho, I.O. Moore, J.A., Alexander, M.S., Scott, K.R.; Journal of Pharmaceutical Sciences, Aug. 1994, 83 (8) pp. 1155–1170.

"Profile of anticonvulsant activity and minimal toxicity of Methyl 4–[ (p–chlorophenyl) amino]–6 . . . "; Mulzac, D., Scott, K.R.; Epilepsia, Nov. –Dec. 1993, 34(6) pp. 1141–1146.

"2,3–Dihydro–4H–1,4–Thiazines and 5,6–Dihydro–3H–Furo [3,4–b]–1,4–Thiazines from 4–Tetrahydropyranyloxyalk–2–Ynenitriles"; Roberts, R.R., Landor, S.R.. Tetrahedron Letters, vol. 34, No. 36, pp. 5681–5684, 1993.

"Synthesis of 2,3–Dihydro–1H–phenothiazin–4(10H)–ones"; Miyano, S., Abe, N. and Sumoto, K.; J.C.S. Chem. Comm., p. 760, 1975.

"Synthesis of Some 5–Substituted 2–Aminobenzenethiols and their conversion into Phenothiazines via Smiles Rearrangement"; Mital R.L., Jain, S.K.; J. Chem Soc. pp. 2148–2150 (1969).

"The Preparation and Characterization of 2–Amino–5, 6–dichloro and 2–Amino–6, 7–dichlorobenzothiazole"; R.J. Alaimo; Apr. 1971, pp. 309–310.

"Studies on Phenothiazines. Part 7(1). Synthesis of 3–Substituted 2–Aminobenzenethiols and their Conversion into Phenothiazines"; Gupta, R.R., Ohja, K.G., Kumar, M.; J. Hetereocyclic Chem. 17, pp. 1325–1328 (1980).

"Synthesis of 5,6–and 5,7–Dichloro–3–methyl–4H–1, 4–benzothiazines and their Conversion into Sulfones"; Gupta, R.R., Saraswat, V., Gupta, v., Rajoria, C.M., Gupta, A., Jain, M.; J. Heterocyclic Chem., 30, 803–806 (1993).

"Condensation of diethyl malonate with methyl vinyl ketone"; Spencer, T.A. Newton, M.D., Baldwin, S.W.; Journal of Organic Chemistry, 1964, 29, 787–789.

"Heterocyclic syntheses via the intramolecular acylation of Enamines . . . "; Friary R.J., Gilligan, J.M., Szajewski, R.P., Falci, K.J. et al.; Journal of Organic Chemistry, 1973, 38(20), pp. 3487–3491.

"Synthesis, Benzodiazepine Receptor Binding, and Anticonvulsant Activity of 2,3–Dihydro–3–oxo–5H–pyrido [3,4–b] [1,4]benzothiazine–4–carbonitriles"; Chorvat, R., Desai, B., Radak, S.E., Bloss, J., Hirsch, J., Tenen, S.; J. Med. Chem. 1983, 26, 845–850.

"The Fischer Indole Synthesis"; Robinson, B., In "Organic Reactions", vol. 1, pp. 373–401, R. Adams, Editor; John Wiley and Sons (1952).

"Substitution and Addition Reaction of Thiocyanogen"; Wood, J.L., In "Organic Reactions", vol. 3, pp. 240–266, R. Adams, Editor; John Wiley and Sons (1957).

"Synthesis of Halogen–Substituted 1,5–Benzothiazepine Derivatives and Their Vasodilating and Hypotensive Activities"; Inoue, H. et al., J. Med. Chem., 1991, 34, 675–687.

(List continued on next page.)

Primary Examiner—Richard L. Raymond
Attorney, Agent, or Firm—Kenyon & Kenyon

[57] ABSTRACT

Phenothiazines of the formula:

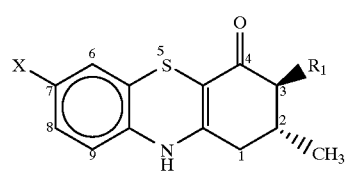

where $R_1$ is H or —COOR, where R is selected from the group consisting of branched or unbranched alkyl groups containing from 1 to 4 carbon atoms, and where X is selected from H, branched or unbranched alkyl groups containing from 1 to 4 carbons, and halogen, and pharmaceutically acceptable salts thereof. Particularly preferred phenothiazines are those wherein X is hydrogen, chloro, bromo or methyl, $R_1$ is COOR, and R is methyl, ethyl or t-butyl.

9 Claims, 2 Drawing Sheet

OTHER PUBLICATIONS

"Reactions of Enamino–ketones. Part II. Synthesis of 4H–1,4–Benzothiazines"; Miyano, S., Abe N., Sumoto, K., Teramto, K.; J.C.S. Perkin I, 1976, pp. 1146–1149.

"Phenalenones. IV(1). Heterocycles from 3–Hydroxyphenalenone (I)"; Kuroki, M., Terachi, Y., Tsunashima, Y.; J. Heterocyclic Chem., Aug. 1981, pp. 873–876.

"Rearrangement of Sulphonium Ylides of the 1H–1,4–Thiazine Type"; Foster, R., Gilchrist, T.L.; J. Chem. Soc. Perkin Trans.I, 1991, pp. 2249–2254.

"A Convenient Preparation of Haloaminobenzo (b) thiophene Derivatives"; Galvez, C., Garcia, F., Veiga, M., Viladoms, P.; Synthesis, Nov. 1983, pp. 932–933.

"Preparation and Some Reactions of 1H–1,–4–Benzothiazine Ylides ( =1H, 1,4–Benzothioniaazin–4–ide)"; Iskander, G.M., Khawad, I.E., Yousif, G, Fisher, K.; Helvetica chimica Acta, vol. 68 (1985), pp. 2216–2225.

"Studies in the Heterocyclic Series. XVIII. Utilization of 4–Aminopyrimidine Chemistry in 1,4,7,9–Tetraazabenzo [b]; phenothiazine Synthesis"; Okafor C.O.; J. Heterocyclic Chem., vol. 17, Nov. 1980, pp. 1587–1592.

"1H–1,4–Benzothiazines. New Cyclic Sulponium Ylides"; Gilchrist, T.L., Iskander, G.M.; J.C.S. Perkin I., Sep. 1982, pp. 831–834.

"Synthesis of 6–Substituted 7,8,9,10–Tetrahydrophenanthridin–7–ones through Sulfur Extrusion"; Matsuo, K., Ohta, M., Tanaka, K.; Chem. Pharm. Bull., 33(9), pp. 4063–4068 (1985).

"Synthesis and Reactions of 11–Substituted 3,3–Dimethyl–2,3,4,5–tetrahydro–1H–dibenzo [b,e][1,4] diazepin–1–ones"; Matsuo, K., Yoshida, M., Ohta, M., Tanaka, K.; Chem. Pharm. Bull., 33(9), pp. 4057–4062 (1985).

"Copper (I) Ioded–Promoted Cyclization of N–2–Haloaryl and N–(2–Haloaryl) Methyl–Substituted Enaminones"; Osuka, A., Mori, Y. and Suzuki, H.; Chemistry Letters, pp. 2031–2034, 1982.

3-CARBOALKOXY-2, 3-DIHYDRO-1H-PHENOTHIAZIN-4[10H]-ONE DERIVATIVES

BACKGROUND OF THE INVENTION

In an attempt to discover analogs of the prototype anticonvulsant methyl 4-[(4'-chlorophenyl)-amino]-6-methyl-2-oxo-3-cyclohexene-1-carboxylate, 1, alkyl 4-[(5'-chloro-2'-pyridinyl)amino]-6-methyl-2-oxo-3-cyclohexene-1-carboxylates, 2 [R=CH$_3$ (2a); R=C$_2$H$_5$ (2b)], and alkyl 4-[(5'-methyl)-3'-isoxazolylamino]-6-methyl-2-oxo-3-cyclohexene-1-carboxylates, 3 [R=CH$_3$ (3a); R=C$_2$H$_5$ (3b); R=C(CH$_3$)$_3$ (3c)], have been targeted. Edafiogho, I. O.; Hinko, C. N.; Chang, H.; Moore, J. A.; Mulzac, D.; Nicholson, J. M.; Scott, K. R. Synthesis and anticonvulsant activity of enaminones. *J. Med. Chem.* 1992, 35, 2798–2805. Scott, K. R.; Edafiogho, I. O.; Richardson, E. L.; Farrar, V. A.; Moore, J. A.; Tietz, E. I.; Hinko, C. N.; Chang, H.; El-Assadi, A; Nicholson, J. M. Synthesis and anticonvulsant activity of enaminones. 2. Further structure activity correlations. *J. Med. Chem.* 1993, 36, 1947–1955. U.S. Pat. No. 5,580,894.

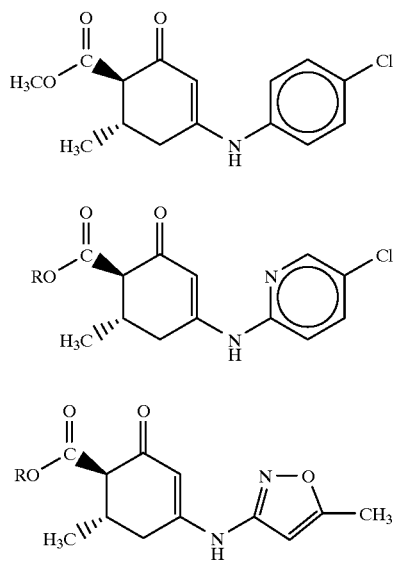

Moreover, the basic phenothiazine ring system has been shown to be an essential pharmacophore for tranquilizers, anticancer agents, antiinflammatory agents, antihistaminics, anthelminics, local anesthetics, antiseptics, growth inhibitors, and in the treatment of neuropsychiatric disorders. (a) Gupta, R. R. Ed. Phenothiazines and 1,4-benzothiazines. Chemical and biomedical aspects. Elsevier, Amsterdam, The Netherlands, 1988. (b) Benz, G.; Fengler, G.; Meyer, H.; Niemers, E.; Fiedler, V.; Mardin, M.; Mayer, D.; Perzbom, E.; Seuter, F. et al. Use of 4H-1,4-benzothiazines in the prevention and therapy of respiratory diseases, inflammations/rheumatism, thromboembolic diseases, ischemias and infarctions, heart rhythm disturbances, arteriosclerosis, and dermatosis, drugs for this purpose, and active substances contained in these drug. *Chem. Abstr.* 1986, 105, 60620y; Ger. Offen. DE 3,426,564. (c) Niemers, E.; Gruetzmann, R.; Mardin, M.; Busse, W. D.; Meyer, H. Annellated 4H-1,4-benzothiazine lipoxygenase inhibitors. *Chem. Abstr.* 1984, 100, 185787k; Ger. Offen. DE 3,229,122. The mechanism for the variety of therapeutic activities is believed to be due to the presence of a fold along the nitrogen-sulfur axis. Gupta, R. R.; Saraswat, V.; Gupta, V.; Rajoria, C. M.; Gupta, A.; Jain, M. Synthesis of 5,6- and 5,7-dichloro-3-methyl-4H-1,4-benzothiazines and their conversion into sulfones. *J. Heterocyclic Chem.* 1993, 30, 803–806. Anticonvulsant activity has been reported for a related series of 2,3-dihydro-3-oxo-5H-pyrido[3,4-b][1,4]benzothiazine-4-carbonitriles. Chorvat, R. J.; Desai, B. N.; Radak, S. E.; Bloss, J.; Hirsch, J.; Tenen, S. Synthesis, benzodiazepine receptor binding, and anticonvulsant activity of 2,3-dihydro-3-oxo-5H-pyrido-[3,4-b][1,4]benzothiazine-4-carbonitriles. *J. Med. Chem.* 1983, 26, 845–850.

SUMMARY OF THE INVENTION

The present invention is directed to a novel series phenothiazines. In particular the present invention is concerned with phenothiazines of the formula:

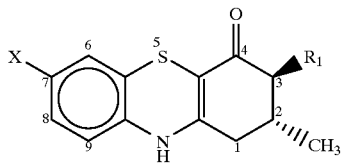

where R$_1$ is H or —COOR, where R is selected from the group consisting of branched or unbranched alkyl groups containing from 1 to 4 carbon atoms, and where X is selected from H, branched or unbranched alkyl groups containing from 1 to 4 carbons, and halogen, and pharmaceutically acceptable salts thereof. Particularly preferred phenothiazines are those wherein X is hydrogen, bromo, chloro or methyl, R$_1$ is COOR, and R is methyl, ethyl or t-butyl.

According to an embodiment of the present invention, a pharmaceutical composition is provided comprising an effective amount of the above phenothiazines and a pharmaceutically acceptable carrier.

According to yet another embodiment of the present invention, a method of treating grand mal and partial seizures in a mammal is provided comprising administering to the mammal an effective amount of the above phenothiazines.

The above phenothiazines are advantageous in that they are central nervous system agents having anticonvulsive activity, with particularly exceptional potency against electroshock seizures.

Due to their biological response, the compounds of the present invention are useful to prevent, alleviate, control or study a variety of diseases and undesirable psychological conditions in mammals, including humans, pets, zoological specimens, domestic animals, and laboratory animals, such as monkeys, rabbits, rats and mice. Such diseases and conditions include epilepsy, parkinsonism, Huntington's chorea and Alzheimers disease.

These and other embodiments and the advantages will become readily apparent upon reading the description, examples and claims to follow.

Unless indicated to the contrary, all references cited herein are incorporated by reference in their entireties.

DETAILED DESCRIPTION

Figure 1:
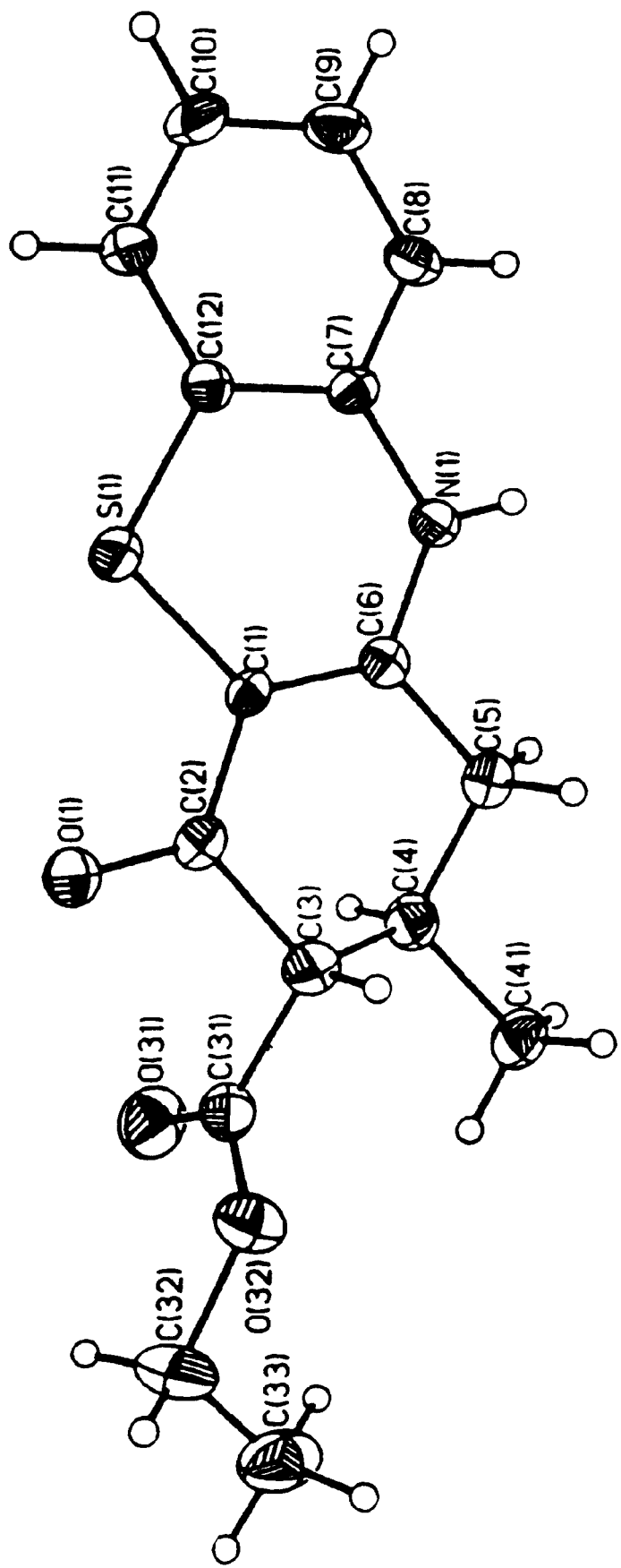
FIG. 1 depicts the X-ray structure of compound 4b (R=C$_2$H$_5$; X=H).

In considering conformationally restricted analogs of 1, analogs having the two positions b- to the enaminic nitrogen linked in a tricyclic structure were explored by the present inventors. The present invention is directed to linkage through a sulfur atom. Hence, a novel series of 3-carboalkoxy-2,3-dihydro-1H-phenothiazin-4[10H]-ones (4a–c and 4e–m) as well as the unsubstituted analog, 4d, have been synthesized. These compounds are listed in Table I.

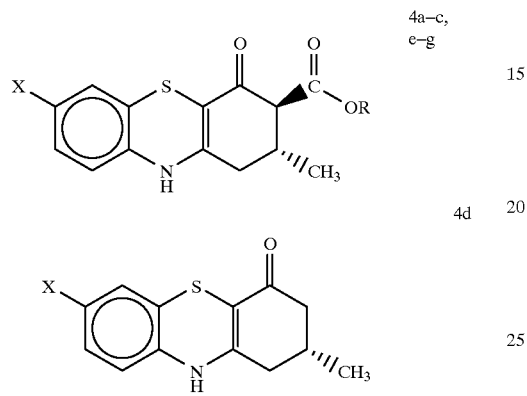

4a–c, e–g

4d

TABLE I

Physical Properties of Phenothiazines

| Compound | R | X | MP, ° C. | Formula |
|---|---|---|---|---|
| 4a | $CH_3$ | H | 218–221 | $C_{15}H_{15}NO_3S$ |
| 4b | $C_2H_5$ | H | 201–202 | $C_{16}H_{17}NO_3S$ |
| 4c | $C(CH_3)_3$ | H | 221–222 | $C_{18}H_{21}NO_3S$ |
| 4d | H | H | 278[a] | $C_{13}H_{13}NOS$ |
| 4e | $CH_3$ | Cl | 226–227 | $C_{15}H_{14}ClNO_3S$ |
| 4f | $C_2H_5$ | Cl | 229–230 | $C_{16}H_{16}ClNO_3S$ |
| 4g | $C(CH_3)_3$ | Cl | 261–262 | $C_{18}H_{20}ClNO_3S$ |
| 4h | $CH_3$ | $CH_3$ | 225[a] | $C_{16}H_{17}NO_3S$ |
| 4i | $C_2H_5$ | $CH_3$ | 244[a] | $C_{17}H_{19}NO_3S$ |
| 4j | $CH_3$ | Br | 186–189 | $C_{13}H_{14}BrNO_3S$ |
| 4k | $C_2H_5$ | Br | 201–203 | $C_{16}H_{16}BrNO_3S$ |
| 4l | $C(CH_3)_3$ | Br | 191–194 | $C_{18}H_{20}BrNO_3S$ |
| 4m | H | Br | 250[a] | $C_{13}H_{11}BrNOS$ |

[a]Compound melted with decomposition.

Synthetic Scheme

Thiazines have been previously synthesized by employing enamines (derived from acetylenic nitriles and esters). Roberts, R. R.; Landor, S. R. 2,3-Dihydro-4H-1,4-thiazines and 5,6-dihydro-3H-furo[3,4-b]-1,4-thiazines from 4-tetrahydropyranyloxyalk-2-ynenitriles. *Tetrahedron Lett.* 1993, 34, 5681–5684. A first scheme for the practice of the present invention is as follows.

Scheme I

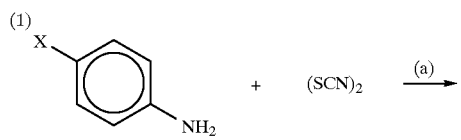

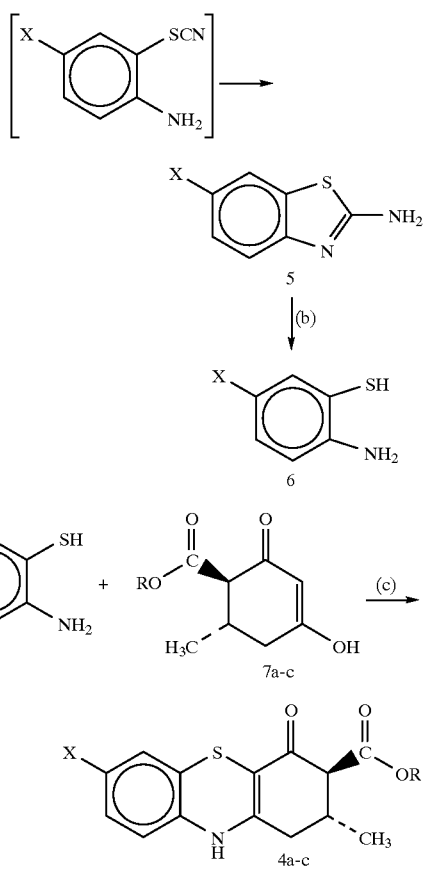

This scheme is believed to follow a classical one-pot reaction of Miyano and co-workers (Miyano, S.; Abe, N.; Sumoto, K. Synthesis of 2,3-dihydro-1H-phenothiazin-4 (10H)-ones. *J. Chem. Soc. Chem. Comm.* 1975, 760) involving the condensation and oxidative cyclization of the appropriately substituted 2-aminobenzenethiols, 6, with the b-dicarbonyl ester, 7 [R=$CH_3$ (7a); R=$C_2H_5$ (7b); R=C($CH_3$)$_3$ (7c)] in refluxing DMSO to provide 4a–c and 4e–l in reasonably pure form. The precursor thiol compounds 6 are derived from the base-catalyzed hydrolytic fission of the 6-substituted-2-aminobenzothiazoles, 5, prepared by the action of potassium (or ammonium) thiocyanate and bromine (generating thiocyanogen, [(SCN)$_2$], in situ), on p-substituted anilines as described in the literature. Mital, R.; Jain, S. K. Synthesis of some 5-substituted 2-aminobenzenethiols and the conversion into phenothiazines via Smiles rearrangement. *J. Chem. Soc. (C)* 1969, 2148–2150.

An alternative scheme for the practice of the present invention is presented below.

Scheme 2

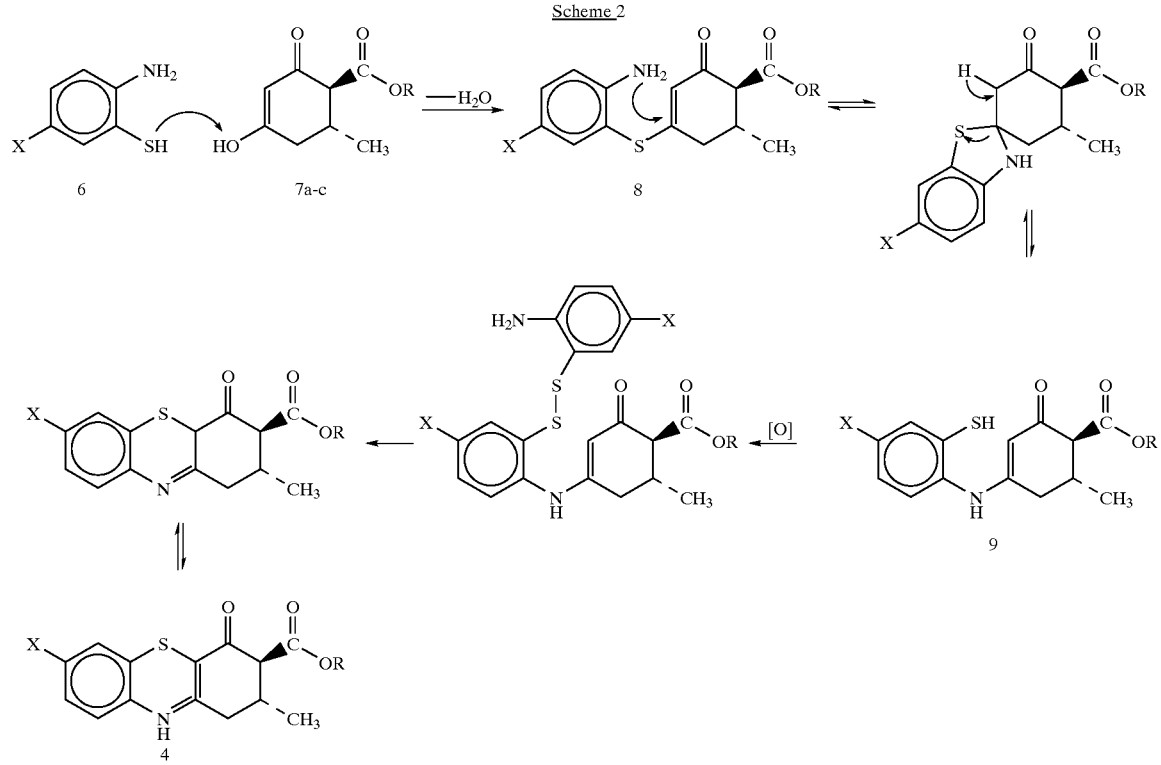

In this alternative scheme a salient mechanistic feature for construction of 4a–c and 4e–1 involves transformation of the ensulfide 8 to enaminic ketone 9 followed by oxidative ring closure of the latter compound. This mechanism type has been proposed. Roberts, R. R.; Landor, S. R. 2,3-Dihydro-4H-1,4-thiazines and 5,6-dihydro-3H-furo[3,4-b]-1,4-thiazines from 4-tetrahydropyranyloxyalk-2-ynenitriles. *Tetrahedron Lett.* 1993, 34, 5681–5684.

Without wishing to be held to any particular theory, when experimental conditions for the final step are identical for each ester, (i.e., 40 min reflux in DMSO), it is believed that the ter-butyl compound 4c (X=H) undergoes thermal decomposition to give 2,3-dihydro-1H-phenothiazin-4 [10H]-one, 4d (X=H). Thermal decomposition of the desired phenothiazine 4c (X=H) to butylene and the b-keto acid (4, R=X=H) is suspected, followed by decarboxylation of the latter compound to 4d (X=H). This is substantiated by the formation of the 4c series by employing shorter reflux times in DMSO. Stability studies of the 3-carbo-ter butoxy-phenothiazine (41, X=Br) confirm the lability of the 3-carbo-ter butoxy substituent with refluxing DMSO for periods up to 40 min, forming 4m (X=Br). Friary and coworkers have shown that 7c (R=C(CH₃)₃) is readily decarboxylated under acid-catalyzed conditions to form 7d (see Scheme III below). Friary, R. J.; Gilligan, J. M.; Szajewski, R. P.; Falci, K. J.; Franck, R. W. Heterocyclic syntheses via the intramolecular acylation of enamines derived from animo acids. *J. Org. Chem.* 1973, 38, 3487–3490.

Scheme III

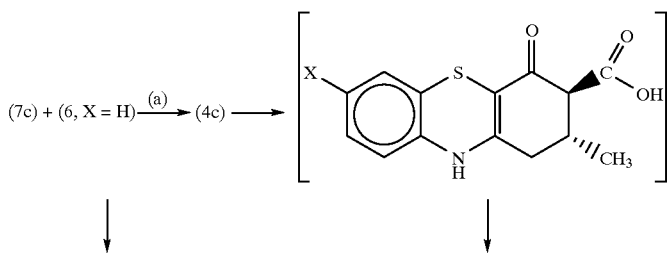

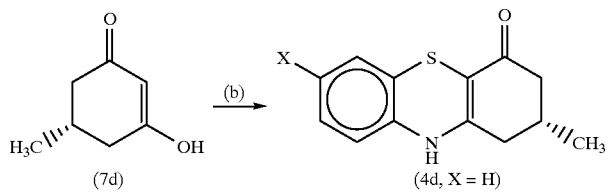

Reaction conditions:
(a) Reflux DMSO; 5-8 min; (b) 6 (X = H), reflux DMSO; 5-8 min.

The compounds of the present invention can be readily provided in the form of pharmaceutically acceptable salts. Suitable pharmaceutically acceptable salts include salts derived from inorganic or organic acids. Typical examples of pharmaceutically acceptable salts include salts derived from inorganic acids such as hydrochloric acid, hydrobromic acid, sulfuric acid, phosphoric acid, nitric acid and the like, and organic acids such as acetic acid, propionic acid, glycolic acid, oxalic acid, pyruvic acid, malic acid, succinic acid, malonic acid, maleic acid, fumaric acid, citric acid, tartaric acid, mandelic acid, cinnamic acid, benzoic acid, p-toluenesulfonic acid, salicylic acid, ethane sulfonic acid, methanesulfonic acid and so forth. The formation of such salts is well within the abilities of those of ordinary skill in the art.

Administration

For each utility and indication, the amount of ingredient required will depend upon a number of factors including the severity of the condition to be treated and the identity of the recipient, and will ultimately be at the discretion of the attendant physician or veterinarian. In general however, for each of these utilities and indications, a suitable effective dose will preferably be in the range 0.1 to 250 mg per kilogram bodyweight of recipient per day, more preferably in the range 0.1 to 10 mg per kilogram bodyweight per day.

While it is possible for the active ingredients to be administered alone it is preferable to present them as pharmaceutical formulations. The formulations, both for veterinary and for human use, of the present invention comprise at least one active ingredient, as defined above, together with one or more acceptable carriers thereof and optionally other therapeutic ingredients. The carrier(s) must be "acceptable" in the sense of being compatible with the other ingredients of the formulation and not deleterious to the recipient thereof.

The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include a step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product into tablet form, for example.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as a bolus, electuary or paste.

A tablet may be made by compression or molding, optionally with one or more pharmaceutically acceptable excipients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding a mixture of the powdered compound moistened with an inert liquid diluent in a suitable machine. The tablets may optionally be coated or scored and may be formulated so as to provide slow or controlled release of the active ingredient therein.

For topical applications, the formulations are preferably applied as an ointment or cream. When formulated in an ointment, the active ingredients may be employed with either a paraffinic or water-miscible ointment base. Alternatively, the active ingredients may be formulated in a cream with an oil-in-water cream base.

If desired, the aqueous phase of the cream base may include, for example, at least 30% w/w of a polyhydric alcohol, i.e., an alcohol having two or more hydroxyl groups such as propylene glycol, butane 1,3-diol, mannitol, sorbitol, glycerol and polyethylene glycol and mixtures thereof. The topical formulations may desirably include a compound which enhances absorption or penetration of the active ingredient through the skin or other affected areas. Examples of such dermal penetration enhancers include dimethylsulfoxide and related analogues.

Formulations suitable for topical administration to the eye also include eye drops wherein the active ingredient is dissolved (or suspended) in a suitable carrier, especially in aqueous solvent for the active ingredient.

Formulations suitable for topical administration in the mouth include lozenges containing the active ingredient, preferably in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising, for example, cocoa butter or a stearate.

Formulations suitable for nasal administration wherein the carrier is a solid include a coarse powder having a particle size, for example, in the range of from about 20 to about 500 microns, which is administered by rapid inhalation through the nasal passage. Suitable formulations wherein the carrier is a liquid, for administration as, for example, a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of the sterile liquid carrier, for example, water for injection, immediately prior to use. Extemporaneous injection solutions and suspensions may be prepared from sterile powders, granules and tablets of the kind previously described. Formulations for intramuscular administration are particularly preferred.

Preferred unit dosage formulations are those containing a daily dose or daily sub-dose, as herein above recited, or an appropriate fraction thereof, of an active ingredient.

It should be understood that, in addition to the ingredients particularly mentioned above, the formulations of this invention may include other agents conventional in the art having regard to the type of formulation in question. For example, those suitable for oral administration may include flavoring agents.

The present invention further provides veterinary compositions containing at least one active ingredient as above defined together with a veterinary carrier thereof Veterinary carriers are materials useful for the purpose of administering the composition and may be solid, liquid or gaseous materials useful for the purpose of administering the composition and are otherwise inert or acceptable in the veterinary art and are compatible with the active ingredient. These veterinary compositions may be administered orally, parenterally or by any other desired route.

For oral administration, the compositions can be in the form of a tablet, granule drench, paste, cachet, capsule or feed supplement. Granules may be made by the well known techniques of wet granulation, precompression or slugging. They can be administered to animals via an inert liquid vehicle so as to form a drench, or in a suspension with water or oil base. Preferably, further accessory ingredients, such as a dispensing agent, are included.

Additional formulation information can be found, for example, in U.S. Pat. No. 5,079,252 the disclosure of which is incorporated by reference in its entirety.

Experimental Section

Melting points are determined on a Thomas-Hoover capillary melting point apparatus and are uncorrected. Results are shown in Table I above. IR spectra are recorded on samples in KBr, as diluted chloroform solutions in matched sodium chloride cells, or neat with a Perkin-Elmer 1330 spectrophotometer, and are shown in Table II.

TABLE II

| | IR Data in KBr Pellets | | | | | |
|---|---|---|---|---|---|---|
| Compound | N—H | C—N | Ester C=O | C—O | C=O | Aromatic Strech |
| 4a | 3258.9 | 1200 | 1735.8 | 1152.9 | 1587.2 | 1514.4 |
| 4b | 3261.1 | 1316.7 | 1738.2 | 1142.6 | 1566.9 | 1513.6 |
| 4c | 3275.3 | 1288.1 | 1726.2 | 1156.9 | 1566.4 | 1511.5 |
| 4d | 3248.4 | 1259.4 | — | — | 1576.8 | 1515.6 |
| 4e | 3256.7 | 1284.3 | 1743.7 | 1143.1 | 1565.5 | 1513.6 |
| 4f | 3256.5 | 1317.5 | 1737.7 | 1141.8 | 1565.5 | 1510.6 |
| 4g | 3278.4 | 1285.3 | 1723.1 | 1155.9 | 1588.3 | 1565.9 |
| 4h | 3254 | 1319.5 | 1740.2 | 1147.4 | 1561.6 | 1500 |
| 4i | 3261.3 | 1318.6 | 1738.4 | 1148.1 | 1562 | 1516.3 |

$^1$H NMR spectra are recorded on a General Electric QE 300-MHz spectrometer in deuterated solvents using tetramethylsilane as an internal reference. The results are shown in Table III.

TABLE III

$^1$H NMR (DMSO-$d_6$) correlation table for 2,3-Dihydro-1H-phenothiazin-4(10H)-ones

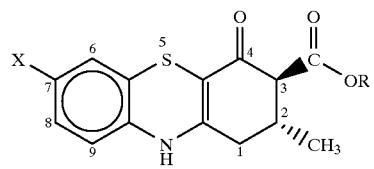

| | | | 4a | 4b | 4c | 4e | 4f | 4g |
|---|---|---|---|---|---|---|---|---|
| | | | R = CH$_3$ | R = C$_2$H$_5$ | R = C(CH$_3$)$_3$ | R = CH$_3$ | R = C$_2$H$_5$ | R = (CH$_3$)$_3$C |
| | | | X = H | X = H | X = H | X = Cl | X = Cl | X = Cl |
| C$_2$—CH$_3$ | | d | 0.93 | 0.93 | 0.95 | 0.94 | 0.93 | 0.94 |
| | | | J = 5.19 | J = 5.13 | J = 5.27 | J = 5.80 | J = 5.79 | J = 5.37 |
| C$_2$—CH and C$_1$—CH$_2$ | | m | 2.32 | 2.31 | 2.29 | 2.30 | 2.30 | 2.27 |
| C$_3$—CH | | d | 3.18 | 3.14 | 2.97 | 3.19 | 3.15 | 2.97 |
| | | | J = 11.22 | J = 11.81 | J = 11.06 | J = 11.37 | J = 11.1 | J = 11.21 |
| C$_9$—CH | | d | 6.57 | 6.56 | 6.56 | 6.54 | ≈6.5 | 6.56 |
| | | | J = 7.80 | J = 7.76 | J = 8.16 | J = 8.30 | J = 8.3 | J = 8.40 |
| N$_{10}$—H | | s | 9.17 | 9.16 | 9.08 | 9.26 | 9.25 | 9.08 |

TABLE III-continued $^1$H NMR (DMSO-$d_6$) correlation table for 2,3-Dihydro-1H-phenothiazin-4(10H)-ones

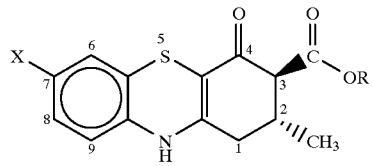

| Aromatic R | m s | 6.76 CH$_3$ | 6.76 CH$_3$ t, 1.19 CH$_2$ q, 4.13 | 6.75 (CH$_3$)$_3$C s, 1.41 | 6.54 CH$_3$ s | 6.88 CH$_3$ t, 1.19 CH$_2$ q, 4.13 | 6.87 (CH$_3$)$_3$C s, 1.41 |
|---|---|---|---|---|---|---|---|

|  |  | 4h | 4i |
|---|---|---|---|
|  |  | R = CH$_3$ X = CH$_3$ | R = C$_2$H$_5$ X = CH$_3$ |
| C$_2$—CH$_3$ | d | 0.94 J = 5.34 | 0.93 J = 5.13 |
| C$_2$—CH and C$_1$—CH$_2$ | m | 2.3 | 2.31 |
| C$_3$—CH | d | 3.19 J = 11.21 | 3.14 J = 11.81 |
| C$_9$—CH | d | 6.49 J = 7.95 | 6.56 J = 7.76 |
| N$_{10}$—H | s | 9.07 | 9.16 |
| Aromatic R | m s | 6.7 CH$_3$ s | 6.76 CH$_3$ t, 1.19 CH$_2$ q, 4.13 |

The stereochemistry about the C$_2$–C$_3$ bond of the phenothiazines 4a–c and 4e–i is confirmed by the $^1$H-NMR spectroscopy which indicates the presence of a methine doublet at ca. d 3.1 with J$_{H-H}$ 11Hz. Hydrogens at C$_{1,2}$ coincide as a 3H multiplet at d 2.3. Assignments to the H$_{8,9}$ aromatic hydrogens an unambiguously made by noting the weak meta-coupling (J=3.0Hz) of H$_{6-8}$. To distinguish between isomeric forms 4 and 5a, a Nuclear Overhauser difference experiment is performed. The configuration of the sulfur atom with respect to the carbonyl carbons is confirmed. In addition, 2D correlation of these and other signals, allowed for $^{13}$C assignments.

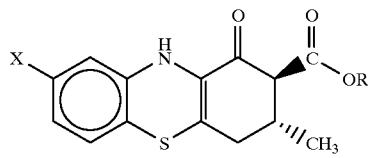

5a

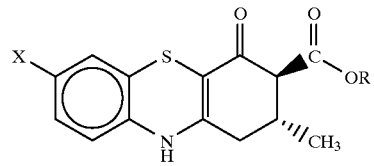

4a–c, e–g $^{13}$C NMR date are recorded on a General Electric QE 300-mHz spectrometer in deuterated solvents using tetramethylsilane as an internal reference and are shown in Table IV.

TABLE IV $^{13}$C NMR (DMSO-$d_6$) Correlation Table for 2,3-Dihydro-1H-phenothiazin-4(10H)-ones.

| Atom | 4a | 4b | 4c | 4e | 4f | 4g | 4h | 4i |
|---|---|---|---|---|---|---|---|---|
|  | R = CH$_3$ X = H | R = C$_2$H$_5$ X = H | R = C(CH$_3$) X = H | R = CH$_3$ X = Cl | R = C$_2$H$_5$ X = Cl | R = C(CH$_3$)$_3$ X = Cl | R = MR X = Me | R = ET X = Me |
| C$_2$—CH$_3$ | 18.71 | 18.59 | 18.18 | 18.64 | 18.52 | 18.42 | 18.62 | 18.61 |
| C$_2$—CH | 30.41 | 30.41 | 30.41 | 30.33 | 30.33 | 30.37 | 30.3 | 30.39 |
| C$_1$—CH$_2$ | 34.25 | 34.24 | 34.23 | 34.16 | 34.15 | 34.15 | 34.18 | 34.24 |
| C$_3$—CH | 59.51 | 59.53 | 60.35 | 59.41 | 59.41 | 60.26 | 59.43 | 59.51 |

TABLE IV-continued $^{13}$C NMR (DMSO-$d_6$) Correlation Table for 2,3-Dihydro-1H-phenothiazin-4(10H)-ones.

| Atom | 4a | 4b | 4c | 4e | 4f | 4g | 4h | 4i |
|---|---|---|---|---|---|---|---|---|
| $C_{4a}$—C—S | 96.55 | 96.60 | 96.73 | 96.26 | 96.29 | 96.41 | 96.1 | 96.16 |
| CH | 115.92 | 115.85 | 115.74 | 116.99 | 116.93 | 116.84 | 115.72 | 115.79 |
| C | 119.58 | 119.57 | 119.54 | 122.31 | 122.27 | 122.27 | 119.38 | 119.43 |
| CH | 124.83 | 124.75 | 124.61 | — | — | — | — | — |
| CH | 126.36 | 126.31 | 126.24 | 125.53 | 125.51 | 125.48 | 126.6 | 126.67 |
| CH | 126.88 | 126.82 | 126.74 | 126.50 | 126.47 | 126.41 | 126.99 | 127.07 |
| C | — | — | — | 128.11 | 128.05 | 127.95 | 133.22 | 133.26 |
| C | 136.00 | 136.02 | 136.11 | 135.07 | 135.07 | 135.18 | 134.01 | 134.07 |
| C | 155.78 | 155.63 | 155.31 | 155.56 | 155.46 | 155.16 | 155.35 | 155.38 |
| C | 170.50 | 169.92 | 169.09 | 170.34 | 169.78 | 168.90 | 170.39 | 169.99 |
| C | 184.07 | 184.12 | 184.50 | 184.13 | 184.22 | 184.67 | 183.66 | 183.88 |
| COOR | 51.53 | 13.97 | 27.59 | 51.52 | 13.94 | 27.58 | 51.36 | 13.98 |
|  | $CH_3$ | $CH_3$ | $CH_3$ | $CH_3$ | $CH_3$ | $CH_3$ | $CH_3$ | $CH_3$ |
|  |  | 60.12 | 80.15 |  | 60.09 | 80.22 |  | 60.05 |
|  |  | $CH_2$ | C |  | $CH_2$ | C |  | $CH_2$ |

Elemental analyses (C, H, N, S and halogen) are performed. The results are shown in Table V, where analyses are indicated only by the symbols of the elements.

TABLE V

Analytical results

| Compound | Empirical Formula | M.W. | Calcd. | Found |
|---|---|---|---|---|
| 4a | $C_{15}H_{15}NO_3S$ | 289.31 | % C 62.27 | % C 62.13 |
|  |  |  | % H 5.24 | % H 5.35 |
|  |  |  | % N 4.84 | % N 5.01 |
|  |  |  | % S 11.06 | % S 11.21 |
| 4b | $C_{16}H_{17}NO_3S$ | 303.34 | % C 63.35 | % C 62.93 |
|  |  |  | % H 5.66 | % H 5.63 |
|  |  |  | % N 4.62 | % N 4.56 |
|  |  |  | % S 10.55 | % S 10.56 |
| 4c | $C_{18}H_{21}NO_3S$ | 331.40 | % C 65.23 | % C 65.19 |
|  |  |  | % H 6.40 | % H 6.44 |
|  |  |  | % N 4.23 | % N 4.37 |
|  |  |  | % S 9.66 | % S 9.70 |
| 4d* | $C_{13}H_{13}NOS$ | 231.27 | % C 67.51 | % C 67.90 |
|  |  |  | % H 5.68 | % H 5.18 |
|  |  |  | % N 6.06 | % N 6.11 |
|  |  |  | % S 13.84 | % S 14.01 |
| 4e | $C_{15}H_{14}ClNO_3S$ | 323.75 | % C 55.64 | % C 55.50 |
|  |  |  | % H 4.37 | % H 4.24 |
|  |  |  | % Cl 10.95 | % Cl 10.92 |
|  |  |  | % N 4.33 | % N 4.38 |
|  |  |  | % S 9.88 | % S 9.86 |
| 4f | $C_{16}H_{16}ClNO_3S$ | 337.78 | % C 56.89 | % C 56.63 |
|  |  |  | % H 4.78 | % H 4.68 |
|  |  |  | % Cl 10.49 | % Cl 10.53 |
|  |  |  | % N 4.15 | % N 4.38 |
|  |  |  | % S 9.47 | % S 9.45 |
| 4g | $C_{18}H_{20}ClNO_3S$ | 365.84 | % C 59.09 | % C 58.80 |
|  |  |  | % H 5.52 | % H 5.49 |
|  |  |  | % Cl 9.69 | % Cl 9.47 |
|  |  |  | % N 3.83 | % N 3.59 |
|  |  |  | % S 8.75 | % S 8.77 |
| 4h | $C_{16}H_{17}NO_3S$ | 303.34 | % C 63.35 | % C 63.29 |
|  |  |  | % H 5.66 | % H 5.69 |
|  |  |  | % N 4.62 | % N 4.68 |
|  |  |  | % S 10.55 | % S 10.88 |
| 4g | $C_{17}H_{19}NO_3S$ | 317.37 | % C 64.33 | % C 64.10 |
|  |  |  | % H 6.05 | % H 5.83 |
|  |  |  | % N 4.41 | % N 4.61 |
|  |  |  | % S 10.08 | % S 10.18 |
| 4h | $C_{16}H_{17}NO_3S$ | 303.34 | % C 63.35 | % C 63.29 |
|  |  |  | % H 5.66 | % H 5.83 |
|  |  |  | % N 4.62 | % N 4.61 |
|  |  |  | % S 10.55 | % S 10.18 |
| 4i | $C_{17}H_{19}NO_3S$ | 317.37 | % C 64.33 | % C 64.10 |
|  |  |  | % H 6.05 | % H 5.83 |
|  |  |  | % N 4.41 | % N 4.61 |
|  |  |  | % S 10.08 | % S 10.18 |
| 4j* | $C_{15}H_{14}BrNO_3S$ | 368.20 | % C 48.93 | % C 49.52 |
|  |  |  | % H 3.84 | % H 3.92 |
|  |  |  | % Br 21.70 | % Br 20.83 |
|  |  |  | % N 3.80 | % N 4.16 |
|  |  |  | % S 8.69 | % S 10.63 |
| 4k* | $C_{16}H_{16}BrNO_3S$ | 382.23 | % C 50.27 | % C 49.17 |
|  |  |  | % H 4.23 | % H 3.92 |
|  |  |  | % Br 20.90 | % Br 20.54 |
|  |  |  | % N 3.67 | % N 4.16 |
|  |  |  | % S 8.37 | % S 10.39 |
| 4l*,a | $C_{18}H_{20}BrNO_3S$ | 410.29 | % C 52.69 | % C 52.11; 52.44; |
|  |  |  | % H 4.92 | % H 5.01; 5.11; |
|  |  |  | % Br 19.47 | % Br 19.00; 19.26; |
|  |  |  | % N 3.41 | % N 3.42; 3.42 |
|  |  |  | % S 7.80 | % S 8.17; 7.79 |
| 4m* | $C_{13}H_{11}BrNOS$ | 310.16 | % c 50.34 | % C 50.86 |
|  |  |  | % H 3.91 | % H 3.96 |
|  |  |  | % Br 25.76 | % Br 25.71 |
|  |  |  | % N 4.52 | % N 4.40 |
|  |  |  | % S 10.32 | % S 10.47 |

*Analytical results differ from theoretical value by >± 0.40%.
$^a$result of a second analysis.

Crystallographic data were also obtained for compound 4b. These data, along with structure refinement are found in Table VIa below. Bond lengths (Å) and angles (°) for compound 4b are found in Table VIb below. Atomic coordinates [×10$^4$] and equivalent isotropic displacement parameters [Å$^2$×10$^3$] are given in Table VIc, where U(eq) is defined as one-third of the orthogonalized $U_{ij}$ tensor. Anisotropic displacement parameter [Å×10$^3$] for compound 4b are presented in Table IVd to follow. The anisotropic displacement factor exponent takes the form: $-2\pi^2[(ha^*)^2U_{11}+...+2hka^*b^*U_{12}]$. Hydrogen coordinates (×10$^4$) and isotropic displacement parameter (Å$^2$×10$^3$) for compound 4b are shown in Table VIe.

Figure 2:
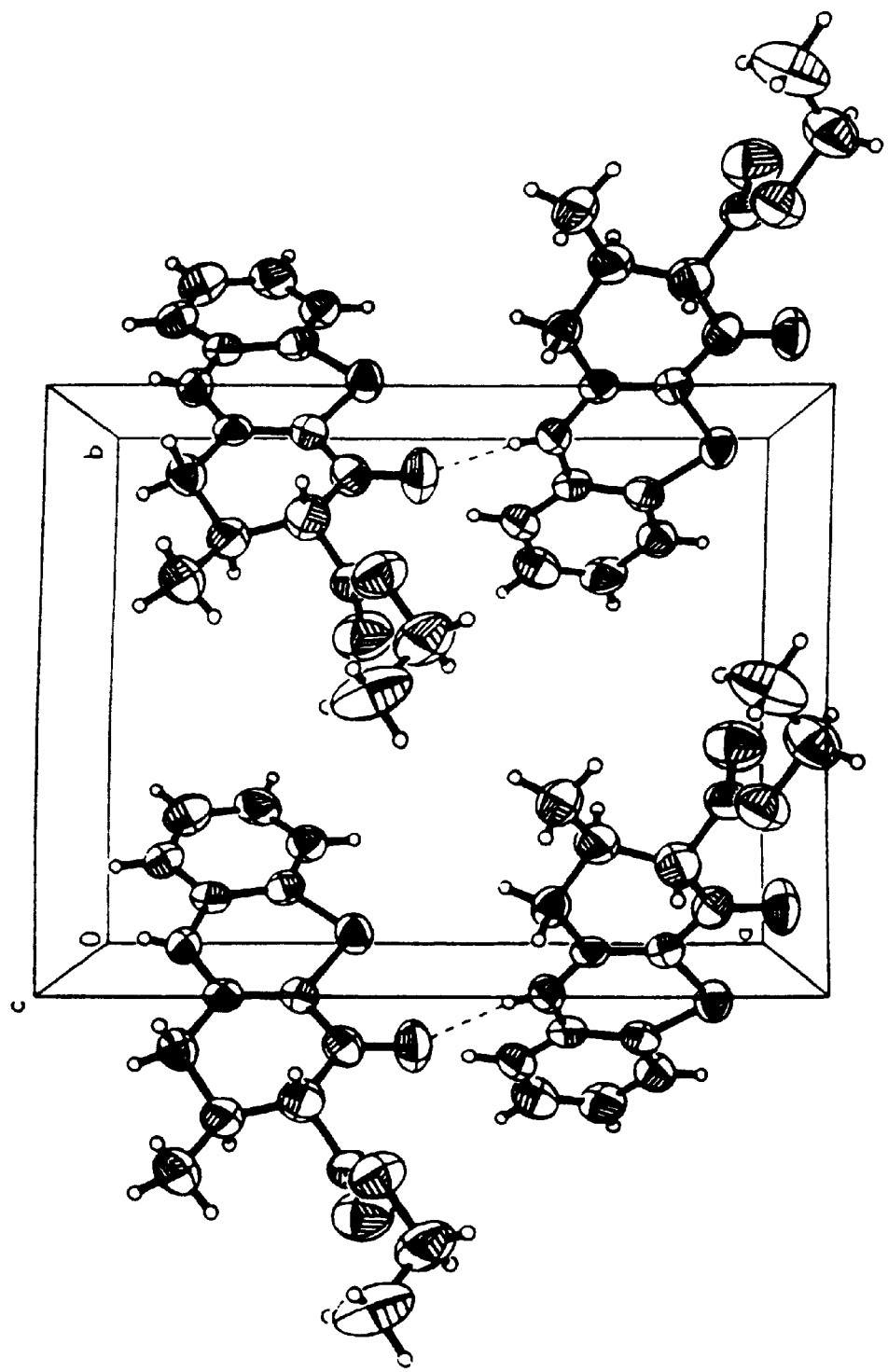
FIG. 2 depicts the X-ray structure of compound 4b in a unit cell.

The X-ray crystal structures determined for compound 4b, alone and within a unit cell, are shown in FIG. 1 and 2, respectively.

TABLE VIa

| | |
|---|---|
| identification code | mll |
| Empirical formula | $CH_{16}H_{17}NO_3S$ |
| Formula weight | 303.37 |
| Temperature | 293(2) K |
| Wavelength | 0.71073 Å |
| Crystal system | Orthorhombic |
| Space group | $Pca2_1$ |
| Unit cell dimensions | a = 13.257(4) Å α = 90* |
| | b = 10.439(3) Å β = 90* |
| | c = 10.875(3) Å γ = 90* |
| Volume | 1505.0 (8) Å$^3$ |
| Z | 4 |
| Density (calculated) | 1.339 Mg/m$^3$ |
| Absorption coefficient | 0.224 mm$^{-1}$ |
| F(000) | 640 |
| Crystal size | 0.13 × 0.52 × 0.26 mm |
| θ range for data collection | 3.07 to 24.99* |
| Index ranges | 0 ≦ h ≦ 15, −12 ≦ k ≦ 0, 0 ≦ M ≦ 12 |
| Reflections collected | 1399 |
| Independent reflection | 1399 ($R_{int}$ = 0.0000) |
| Refinement method | Full-matrix least-square on F$^2$ |
| Data/restraints/parameter | 1399/1/211 |
| Goodness-of-fit on F$^2$ | 1.067 |
| Final R indices [I > 2σ(I)] | R1 = 0.0576, wR2 = 0.1177 |
| R indices (all data) | R1 = 0.1026, wR2 = 0.1419 |
| Absolute structure parameter | −0.1 (2) |
| Larest diff. peak and hole | 0.284 and −0.208 eÅ$^{-3}$ |

TABLE VIb.

| | | | |
|---|---|---|---|
| S(1)-C(1) | 1.772(7) | S(1)-C(12) | 1.780(7) |
| O(1)-C(2) | 1.240(7) | O(31)-C(31) | 1.217(11) |
| O(32)-C(31) | 1.289(11) | O(32)-C(32) | 1.475.(10) |
| N(1)-C(6) | 1.355(9) | N(1)-C(7) | 1.396(9) |
| C(1)-C(6) | 1.365(8) | C(1)-C(2) | 1.417(10) |
| C(2)-C(3) | 1.534(11) | C(3)-C(4) | 1.480(11) |
| C(3)-C(31) | 1.505(11) | C(32)-C(33) | 1.460(14) |
| C(4)-C(5) | 1.489(11) | C(4)-C(41) | 1.521(11) |
| C(5)-C(6) | 1.508(10) | C(7)-C(8) | 1.385(10) |
| C(7)-C(12) | 1.418(9) | C(8)-C(9) | 1.378(12) |
| C(9)-C(10) | 1.368(11) | C(10)-C(11) | 1.393(12) |
| C(11)-C(12) | 1.373(11) | | |
| C(1)-S(1)-C(12) | 100.6(3) | C(31)-O(32)-C(32) | 117.7(9) |
| C(6)-N(1)-C(7) | 126.9(6) | C(5)-C(1)-C(2) | 121.6(7) |
| C(6)-C(1)-S(1) | 125.3(6) | C(2)-C(1)-S(1) | 113.1(5) |
| O(1)-C(2)-C(1) | 122.3(7) | O(1)-C(2)-C(3) | 119.5(7) |
| C(1)-C(2)-C(3) | 117.9(6) | C(4)-C(3)-C(31) | 114.0(8) |
| C(4)-C(3)-C(2) | 112.9(7) | C(31)-C(3)-C(2) | 110.4(7) |
| O(31)-C(31)-O(32) | 124.1(8) | O(31)-C(31)-C(3) | 122.4(9) |
| O(32)-C(31)-C(3) | 113.5(9) | C(33)-C(32)-O(32) | 110.5(9) |
| C(3)-C(4)-C(5) | 113.0(8) | C(3)-C(4)-C(41) | 112.6(7) |
| C(5)-C(4)-C(41) | 111.9(7) | C(4)-C(5)-C(6) | 113.0(6) |
| N(1)-C(6)-C(1) | 122.0(7) | N(1)-C(6)-C(5) | 115.8(6) |
| C(1)-C(6)-C(5) | 122.1(7) | C(8)-C(7)-N(1) | 119.3(7) |
| C(8)-C(7)-C(12) | 118.9(7) | N(1)-C(7)-C(12) | 121.8(7) |
| C(9)-C(8)-C(7) | 120.7(8) | C(10)-C(9)-C(8) | 120.4(9) |
| C(9)-C(10)-C(11) | 119.9(9) | C(12)-C(11)-C(10) | 120.6(7) |
| C(11)-C(12)-C(7) | 119.4(7) | C(11)-C(12)-S(1) | 118.3(5) |
| C(7)-C(12)-S(1) | 122.3(6) | | |

Symmetry transformations used to generate equivalent atoms:

TABLE VIc.

| | x | y | z | U(eq) |
|---|---|---|---|---|
| S(1) | 1126(1) | 605(2) | 5(2) | 56(1) |
| O(1) | 303(3) | −1214(6) | 1659(6) | 80(2) |
| O(31) | 977(5) | −4045(7) | 2390(7) | 98(2) |
| O(32) | 747(4) | −3053(6) | 4167(7) | 81(2) |
| N(1) | 3451(5) | 429(7) | 430(6) | 53(2) |
| C(1) | 1843(5) | −404(7) | 983(6) | 43(2) |
| C(2) | 1237(5) | −1213(8) | 1723(7) | 55(2) |
| C(3) | 1762(6) | −2013(9) | 2718(10) | 68(2) |
| C(31) | 1116(6) | −3139(8) | 3074(10) | 64(2) |

TABLE VIc.-continued

| | x | y | z | U(eq) |
|---|---|---|---|---|
| C(32) | 145(9) | −4139(10) | 4628(12) | 101(4) |
| C(33) | 782(12) | −5035(12) | 5305(11) | 116(4) |
| C(4) | 2811(5) | −2358(9) | 2391(9) | 66(3) |
| C(41) | 3337(6) | −3115(10) | 3399(9) | 72(3) |
| C(5) | 3421(5) | −1237(9) | 1986(7) | 54(2) |
| C(6) | 2869(4) | −386(7) | 1091(7) | 44(2) |
| C(7) | 3139(5) | 1222(7) | −532(6) | 44(2) |
| C(8) | 3857(6) | 1854(8) | −1230(8) | 61(2) |
| C(9) | 3574(7) | 2654(9) | −2177(10) | 72(2) |
| C(10) | 2578(8) | 2792(8) | −2479(10) | 73(2) |
| C(11) | 1844(6) | 2126(8) | −1822(7) | 56(2) |
| C(12) | 2107(5) | 1366(7) | −842(7) | 49(2) |

TABLE VId.

| | U11 | U22 | U33 | U23 | U13 | U12 |
|---|---|---|---|---|---|---|
| S(1) | 49(1) | 63(1) | 56(1) | 9(1) | −5(1) | 3(1) |
| O(1) | 46(3) | 103(4) | 91(4) | 35(4) | −5(3) | O(3) |
| O(31) | 118(5) | 82(5) | 92(5) | −10(4) | −19(4) | −8(4) |
| O(32) | 91(4) | 69(4) | 84(5) | 3(4) | 13(4) | −14(3) |
| N(1) | 44(3) | 49(5) | 66(5) | 12(3) | −5(3) | −4(3) |
| C(1) | 49(3) | 43(5) | 35(4) | −2(4) | −6(3) | 3(3) |
| C(2) | 56(4) | 58(4) | 52(5) | 5(4) | −6(4) | 5(4) |
| C(3) | 65(4) | 68(6) | 70(6) | 16(6) | −6(4) | −2(5) |
| C(31) | 67(5) | 48(6) | 78(7) | 5(5) | −10(6) | −1(4) |
| C(32) | 108(7) | 86(8) | 108(10) | 28(7) | 25(7) | −23(7) |
| C(33) | 185(12) | 86(8) | 78(9) | 9(7) | −8(9) | −50(9) |
| C(4) | 63(5) | 55(6) | 80(7) | 8(6) | −14(5) | O(4) |
| C(41) | 67(5) | 73(7) | 77(7) | 10(6) | −15(5) | 11(5) |
| C(5) | 51(4) | 58(5) | 52(5) | −8(4) | −1(4) | 6(4) |
| C(6) | 53(4) | 34(4) | 44(4) | −13(4) | O(3) | 1(3) |
| C(7) | 57(4) | 36(4) | 40(4) | −1(4) | −4(3) | 2(3) |
| C(8) | 60(4) | 51(5) | 71(6) | 8(5) | 3(4) | −11(4) |
| C(9) | 86(6) | 70(6) | 59(5) | 14(6) | 13(5) | −16(5) |
| C(10) | 87(5) | 58(5) | 73(6) | 20(6) | −16(5) | 9(6) |
| C(11) | 61(4) | 55(5) | 53(5) | 6(5) | −3(4) | −2(4) |
| C(12) | 58(4) | 44(5) | 45(5) | −4(4) | −2(3) | −5(3) |

TABLE VIe.

| | x | y | z | U(eq) |
|---|---|---|---|---|
| H(1N) | 3990(57) | 568(78) | 546(86) | 75(31) |
| H(3A) | 1806(6) | −1465(9) | 3448(10) | 81 |
| H(32A) | −385(9) | −3823(10) | 5163(12) | 122(40) |
| H(32B) | −170(9) | −4578(10) | 3942(12) | 206(79) |
| H(33A) | 404(20) | −5794(28) | 5492(51) | 105(35) |
| H(33B) | 1005(39) | −4642(25) | 6056(30) | 78(27) |
| H(33C) | 1357(29) | −5258(49) | 4813(26) | 326(127) |
| H(4A) | 2766(5) | −2931(9) | 1679(9) | 112(39) |
| H(41A) | 2882(16) | −3745(38) | 3724(37) | 119(41) |
| H(41B) | 3541(38) | −2543(13) | 4045(26) | 88(31) |
| H(41C) | 3921(26) | −3534(45) | 3065(15) | 134(46) |
| H(5A) | 4037(5) | −1542(9) | 1604(7) | 87(28) |
| H(5B) | 3609(5) | −736(9) | 2702(7) | 59(21) |
| H(8A) | 4538(6) | 1737(8) | −1058(8) | 68(23) |
| H(9A) | 4063(7) | 3103(9) | −2613(10) | 183(61) |
| H(10A) | 2391(8) | 3330(8) | −3121(10) | 117(36) |
| H(11A) | 1170(6) | 2196(8) | −2049(7) | 67(25) |

Synthesis ter Butyl 6-methyl-2,4-dioxocyclohexane carboxylate, methyl 6-methyl-2,4-dioxo-cyclohexane carboxylate, ethyl 6-methyl-2,4-dioxocyclohexane carboxylate, 5-chloro-2-aminobenzenethiol, 5-methyl-2-aminobenzenethiol, and 5-bromo-2-aminobenzenethiol are prepared by literature methods. Friary, R. J.; Gilligan, J. M.; Szajewski, R. P.; Falci, K. J.; Franck, R. W. Heterocyclic syntheses via the intramolecular acylation of enamines derived from animo acids. *J. Org. Chem.* 1973, 38, 3487–3490. Edafiogho, I. O.;

Hinko, C. N.; Chang, H.; Moore, J. A.; Mulzac, D.; Nicholson, J. M.; Scott, K. R. Synthesis and anticonvulsant activity of enaminones. *J. Med Chem.* 1992, 35, 2798–2805. Spencer, T. A.; Newton, M. D.; Baldwin, S. W. Condensation of diethyl malonate with methyl vinyl ketone. *J. Org. Chem.* 1964, 29, 787–789. Mital, R.; Jain, S. K. Synthesis of some 5-substituted 2-aminobenzenethiols and the conversion J into phenothiazines via Smiles rearrangement. *J. Chem. Soc. (C)* 1969, 2148–2150. 2-Aminothiophenol, sodium, ethyl crotonate, methyl acetoacetate, ethyl acetoacetate, tert butyl acetoacetate, potassium thiocyanate, 4-chloroaniline, p-toluidine, and bromine are obtained from Aldrich Chemical Company and used without purification.

Methyl 6-methyl-2,4-dioxo-cyclohexane carboxylate (7a).

To a freshly prepared solution of sodium (17.78 g, 0.77 gram-atom) in methanol (220 mL) is added methyl acetoacetate 89.66 g (0.77 mole) and the mixture is stirred on an ice bath 15 min after the addition. Ethyl crotonate (100 mL of a 96% product≈88.13 g (100%; 0.77 mole) is added dropwise and the mixture is stirred at room temperature for an additional 30 min. After refluxing (2 h), methyl 6-methyl-2,4-dioxo-cyclohexane carboxylate enolate, which separates, is filtered, and the solid residue is dissolved in a minimum amount of cold water. The aqueous solution acidifed with sulfuric acid (500 mL of a 2 M solution), the precipitate extracted with dichloromethane (4×300 mL) and the organic phase dried over sodium sulfate. The residue is evaporated and the residue recrystallized from toluene to give the title compound: yield, 37 g, 40%, mp 122–123° C. The mother liquor from the reaction is evaporated to dryness, dissolved in cold water and extracted with dichloromethane (after acidification with the same 2 M sulfuric acid used previously). After evaporation and recrystallization from toulene, the mp is identical to the original crop. Total yield: 47 g; 51%.

Ethyl 6-methyl-2, 4-dioxocyclohexane caboxylate (7b).

The same procedure used above is modified using an equivalent amount of anhydrous ethanol as the solvent and ethyl acetoacetate; yield 93.4 g (47%); mp 89–91° C. (from ethyl acetate: petroleum ether, bp 54° C.).

ter Butyl 6-methyl-2, 4-dioxocyclohexane caboxylate (7c).

The same procedure used above is modified using an equivalent amount of anhydrous ethanol as the solvent and tert butyl acetoacetate; yield 90.2 g (44%); mp 145–146° C. (lit. mp 130–131.5°) from acetone: water.

5-Chloro-2-aminobenzenethiol (6, X=Cl).

Potassium thiocyanate (38.8 g, 0.40 mole) and 4-chloroaniline (50.9 g, 0.40 mole) are dissolved in 300 mL of glacial acetic acid. The solution is cooled below 10° C. in an ice bath and while stirring, bromine (10 mL, 0.40 mole) in glacial acetic acid (50 mL) is added dropwise over one hour with the temperature maintained below 10° C. with external cooling. Stirring is continued for an additional 30 minutes. The reaction mixture is stirred at room temperature for 16 hours. The hydrobromide salt of 2-amino-6-chlorobenzothiazole 5 (X=Cl) is washed with hexane (2×25 mL). The salt is dissolved in warm water (300 mL) and the product precipitated by addition of dilute (10%) sodium hydroxide. The crude product is filtered and recrystallized from ethanol (mp 198–200° C., yield 16.47 g, 63.3%). A mixture of 2-amino-6-chlorobenzothiazole 5 (15 g, 0.08 mole), potassium hydroxide (75 g, 1.34 mole), and water (150 mL) is heated with stirring under reflux over nitrogen for 8 hours. The vigorous reaction subsides slowly. The mixture is then diluted with water (20 mL) and filtered. To the filtrate is added 5 N acetic acid with vigorous stirring and cooling until it is just acid to pH paper. The yellow crystals are filtered, washed with cold water and recrystallized from absolute ethanol and decolorized with neutral Norit. Yield of 5-chloro-2-aminobenenethiol (6, X=Cl); 40%; mp 108–110° C. (lit 110° C.).

5-Methyl-2-aminobenzenethiol (6, X=CH$_3$).

The same procedure is repeated with p-toluidine to yield 2-amino-6-methylbenzothiazole 5 (X=CH$_3$) 12.47 g (87.4%); mp 128–130° C. from methanol. 5-Methyl-2-aminobenzenethiol (6, X=CH$_3$) is prepared in 38% yield by potassium hydroxide catalyzed hydrolysis for 8 hours; mp 112–113° C. (lit. 113–115° C.) from absolute ethanol.

5-Bromo-2-aminobenzenethiol (6, X=Br).

The same procedure was repeated with p-bromoaniline to yield 2-amino-6-bromobenzothiazole 5 (X=Br) 21.47 g (94.4%); mp 213–214° C. from methanol. 5-Bromo-2-aminobenzenethiol (6, X=Br) was prepared in 38% yield by the potassium hydroxide catalyzed hydrolysis for 8 hours; mp 112–113° C. (lit. 113–115° C.) from absolute ethanol.

3-Carbomethoxy-2-methyl-2,3-dihydro-1H-phenothiazin-4[10H] -one (4a, R=H).

A mixture of methyl 6-methyl-2,4-dioxocyclohexane-1-carboxylate, 7a (5.52 g, 30 mmole) and 2-aminothiophenol, 6 (X=H, 3.75 g, 30 mmole), in DMSO (10 mL) is placed in a preheated heating mantle. The reaction mixture is stirred and refluxed for 0.5 h. Upon cooling, the reaction mixture forms a solid. The crystals are filtered and the remaining mother liquid is poured into cold water, whereupon further precipitation occurs. Each precipitate is separately recrystallized twice from MeOH and proves to be identical. An analytical sample of 4a, (R=H), mp 218–221° C. occurs as light orange crystals; yield: 1.47 g (55.0%).

3-Carbethoxy-2-methyl-2,3-dihydro-1H-phenothiazin-4[10H] -one (4b, R=H).

A mixture of ethyl 6-methyl-2,4-dioxocyclohexane-1-carboxylate, 7b (5.94 g, 30 mmole) and 2-aminothiophenol, 6 (X=H, 3.75 g, 30 mmole) in DMSO (10 mL) is placed in a preheated heating mantle. The reaction mixture is stirred and refluxed for 0.5 h. Upon cooling, the reaction mixture forms a solid. The crystals are filtered and the remaining mother liquid is poured into cold water, whereupon further precipitation occurs. Each precipitate is separately recrystallized twice from EtOH and proves to be identical. An analytical sample of 4b, (R=H), mp 201–202° C. occurs as light orange crystals; yield: 1.80 g (30.8%).

3-Carbo-ter-butoxy-2-methyl-2,3-dihydro-1H-phenothiazin-4[10H]-one (4c, R=H).

A mixture of ter butyl 6-methyl-2,4-dioxocyclohexane-1-carboxylate, 7c (3.10 g, 14 mmole) and 2-aminothiophenol, 6 (X=H, 1.72 g, 14 mmole) in DMSO (10 mL) is placed in a preheated heating mantle. The reaction mixture is stirred and refluxed for 10 min. Upon cooling, the reaction mixture forms a solid. The crystals are filtered and the remaining mother liquid is poured into cold water, whereupon further precipitation occurs. Each precipitate is separately recrystallized twice from MeOH and proves to be identical. An analytical sample of 4c, (R=H), mp 221–222° C. occurs as light orange crystals; yield: 2.10 g (48.6%).

7- Chloro-3-carbomethoxy-2-methyl-2,3-dihydro-1H-phenothiazin-4[10H] -one (4e, R=Cl).

A mixture of methyl 6-methyl-2,4-dioxocyclohexane-1-carboxylate, 7a (2.53 g, 13.7 mmole) and 5-chloro-2-aminobenzenethiol, 6 (X=Cl, 2.20 g, 13.7 mmole), in DMSO (10 mL) is placed in a preheated heating mantle. The reaction mixture is stirred and refluxed for 0.5 h. Upon cooling, the reaction mixture forms a solid. The crystals are filtered and the remaining mother liquid is poured into cold water, whereupon further precipitation occurs. Each precipitate is separately recrystallized twice from MeOH and proves to be identical. An analytical sample of 4e, (R=Cl), mp 226–227° C. occurs as light orange crystals; yield: 1.70 g (36.7%).

7-Chloro-3-carbethoxy-2-methyl-2,3-dihydro-1H-phenothiazin-4[10H] -one (4f, R=Cl).

A mixture of ethyl 6-methyl-2,4-dioxocyclohexane-1-carboxylate, 7b (2.6 g, 13.1 mmole) and 5-chloro-2-aminobenzenethiol, 6 (X=Cl, 2.0 g, 13.1 mmole) in DMSO (10 mL) is placed in a preheated heating mantle. The reaction mixture is stirred and refluxed for 0.5 h. Upon cooling, the reaction mixture forms a solid. The crystals are filtered and the remaining mother liquid is poured into cold water, whereupon further precipitation occurs. Each precipitate is separately recrystallized twice from EtOH and proves to be identical. An analytical sample of 4f, (R=Cl), mp 229–230° C. occurs as light orange crystals; yield: 2.05 g (49.4%).

7-Chloro-3-carbo-ter-butoxy-2-methyl-2,3-dihydro-1H-phenothiazin-4[10H]-one (4g, R=Cl).

A mixture of ter butyl 6-methyl-2,4-dioxocyclohexane-1-carboxylate, 7c (1.42 g, 6.3 mmole) and 5-chloro-2-aminobenzenethiol, 6 (X=Cl, 1.00 g, 6.3 mmole) in DMSO (10 mL) is placed in a preheated heating mantle. The reaction mixture is stirred and refluxed for 10 min. Upon cooling, the reaction mixture forms a solid. The crystals are filtered and the remaining mother liquid is poured into cold water, whereupon further precipitation occurs. Each precipitate is separately recrystallized twice from MeOH and proves to be identical. An analytical sample of 4g, (R=Cl), mp 261–262° C. occurs as light orange crystals; yield: 1.12 g (50.9%).

3-Carbomethoxy-2,7-dimethyl-2,3-dihydro-1H-phenothiazin-410H)-one (4h, R=Me).

A mixture of methyl 6-methyl-2,4-dioxocyclohexane-1-carboxylate, 7a (0.83 g, 4.5 mmole) and 5-methyl-2-aminobenzenethiol, 6 (X=Me, 0.83 g, 4.5 mmole) in DMSO (10 mL) is placed in a preheated heating mantle. The reaction mixture is stirred and refluxed for 0.5 h. Upon cooling, the reaction mixture forms a solid. The crystals are filtered and the remaining mother liquid is poured into cold water, whereupon further precipitation occurs. Each precipitate is separately recrystallized twice from MeOH and proves to be identical. An analytical sample of 4h, (R=Me), mp 225° C. occurs as light orange crystals; yield: 0.39 g (21.7%).

3-Carbethoxy-2,7-dimethyl-2,3-dihydro-1H-phenothiazin-4[10H]-one (4i, R=Me).

A mixture of ethyl 6-methyl-2,4-dioxocyclohexane-1-carboxylate, 7b (1.43 g, 7.2 mmole) and 5-methyl-2-aminobenzenethiol, 6 (X=Me, 1.0 g, 7.2 mmole) in DMSO (10 mL) is placed in a preheated heating mantle. The reaction mixture is stirred and refluxed for 0.5 h. Upon cooling, the reaction mixture forms a solid. The crystals are filtered and the remaining mother liquid is poured into cold water, whereupon further precipitation occurs. Each precipitate is separately recrystallized twice from EtOH and proves to be identical. An analytical sample of 4i, (R=Me), mp 224° C. occurs as light orange crystals; yield: 0.50 (21.9%).

2-Methyl-2,3-dihydro-1H-phenothiazin-4[10H] -one (4d, R=H).

A mixture of ter butyl 6-methyl-2,4-dioxocyclohexane-1-carboxylate, 7c (3.09 g, 13.7 mmole) and 2-aminothiophenol, 6 (X=H, 1.71 g, 13.7 mmole) in DMSO (10 mL) is placed in a preheated heating mantle. The reaction mixture is stirred and refluxed for 0.5 h. Upon cooling, the reaction mixture forms a solid. The crystals are filtered and the remaining mother liquid is poured into cold water, whereupon further precipitation occurs. Each precipitate was separately recrystallized twice from MeOH and proves to be identical. An analytical sample of 4d, (R=H), mp 278° C. occurs as light orange crystals; yield: 0.46 g (15.4%).

7-Bromo-3-carbomethoxy-2-methyl-2,3-dihydro-1H-phenothiazin-4[10H]-one (4j, R=Br)

A mixture of methyl 6-methyl-2,4-dioxocyclohexane-1-carboxylate, 7a (1.43 g, 7.7 mmole) and 5-bromo-2-aminobenzenethiol, 6 (X=Br, 1.44 g, 7.7 mmole) in DMSO (10 mL) is placed in a preheated heating mantle. The reaction mixture is stirred and refluxed for 0.5 h. Upon cooling, the reaction mixture forms a solid. The crystals are filtered and the remaining mother liquid is poured into cold water, whereupon further precipitation occurs. Each precipitate is separately recrystallized twice from MeOH and proves to be identical. An analytical sample of 4j, (R=Br), mp 186–189° C. occurs as light orange crystals; 0.14 g (13.9%).

7-Bromo-3-carbethoxy-2-methyl-2,3-dihydro-1H-phenothiazin-4[10H]-one (4k, R=Br)

A mixture of ethyl 6-methyl-2,4-dioxocyclohexane-1-carboxylate, 7b (5.94 g, 30 mmole) and 5-bromo-2-aminobenzenethiol, 6 (X=Br, 5.8 g, 30 mmole) in DMSO (10 mL) is placed in a preheated heating mantle. The reaction mixture is stirred and refluxed for 0.5 h. Upon cooling, the reaction mixture forms a solid. The crystals are filtered and the remaining mother liquid is poured into cold water, whereupon further precipitation occurs. Each precipitate is seperately recrystallized twice from MeOH and proves to be identical. An analytical sample of 4k, (R=Br), mp 201–203° C. occurs as light orange crystals; 2.24 g (56.7%).

7-Bromo-3-carbo-ter-butoxy-2-methyl-2,3-dihydro-1H-phenothiazin-4[10H]-one (41, R=Br)

A mixture of ter butyl 6-methyl-2,4-dioxocyclohexane-1-carboxylate, 7c (1.42 g, 6.3 mmole) and 5-bromo-2-aminobenzenethiol, 6 (X=Br, 1.0 g, 4.5 mmole) in DMSO (10 mL) is placed in a preheated heating mantle. The reaction mixture is stirred and heated at 155° C. for 10 minutes. Upon cooling, the reaction mixture forms a solid. The crystals are filtered and the remaining mother liquid is poured into cold water, whereupon further precipitation occurs. Each precipitate is separately recrystallized twice from MeOH and proves to be identical. An analytical sample of 4l, R=Br, mp 191–194° C. occurs as light orange crystals; 1.99 g (77%).

7-Bromo-2-methyl-2,3-dihydro-1H-phenothiazin-4[10H]-one(4m, R=Br)

A mixture of 7-bromo-3-carbo-ter-butoxy-2-methyl-2,3-dihydro-1H-phenothiazin-4[10H]-one (4l R=Br, 3.09 g, 13.7 mmole) in DMSO (10 mL) is placed in a preheated heating mantle. The reaction mixture is stirred and refluxed for 3 h. Upon cooling, the reaction mixture forms a solid. The crystals are filtered and the remaining mother liquid is poured into cold water, whereupon further precipitation occurs. Each precipitate is separately recrystallized twice from MeOH and proves to be identical. An analytical sample of 4m, (R=Br), mp 250° (dec.) occurs as light orange crystals, 2.67 g (63.2%).

Pharmacology

Initial evaluations for anticonvulsant activity include phases I, VIA and VIB test procedures. These tests are performed intraperitoneally in male Carworth Farms No. 1 (CF1) mice, weighing 18–25 g (Phase I) or orally in male Sprague-Dawley rats, weighing 100–150 g (Phases VIA and VIB). The evaluation is based on three tests: maximal electroshock (MES), subcutaneous (scMet), and the rotorod test for neurological toxicity (Tox). (a) Anticonvulsant Screening Project, Antiepileptic Drug Development Program, National Institutes of Health, DHEW Publ (NIH)

(U.S.) 1978, NIH 78–1093. (b) Porter, R. J.; Cereghino, J. J.; Gladding, G. D.; Hessie, B. J.; Kupferberg, H. J.; Scoville, B.; White, B. G. Antiepileptic drug development program. *Cleveland Clin. Q.* 1984, 51, 293–305. (c) Krall, R. L.; Penry, J. K.; White, B. G.; Kupferberg, H. J.; Swinyard, E. A. Antiepileptic drug development: II. Anticonvulsant drug screening. *Epilepsia* 1978, 19, 400–428. In the MES test, maximal electroshock seizures are elicited with a 60- cycle alternating current of 50 mA intensity (5–7 times that necessary to elicit minimal electroshock seizures) delivered via corneal electrodes for 0.2 seconds. A drop of 0.9% saline is placed on the eye prior to application of the electrodes in order to prevent the death of the animal. Abolition of the hind limb tonic extension component of the seizure is defined as protection and results are expressed as the number of animals protected/the number of animals tested.

In the sc MET test, eighty-five mg/kg of pentylenetetrazol, which induces seizures in more than 95% of mice, is administered as a 0.5% solution subcutaneously in the posterior midline. The animal is observed for 30 minutes. Failure to observe even a threshold seizure (a single episode of clonic spasms of at least 5 seconds duration) is defined as protection and the results are expressed as the number of animals protected/ the number of animals tested.

The rotorod test is used to evaluate neurotoxicity. The animal is placed on a 1 inch diameter knurled plastic rod rotating at 6 rpm. Normal mice can remain on a rod rotating at this speed indefinitely. Neurologic toxicity is defined as the failure of the animal to remain on the rod for 1 minute and the results are expressed as the number of animals exhibiting toxicity/the number of animals tested.

In phase I, compounds are suspended in 0.5% aqueous methylcellulose and are administered intraperitoneally at three dosage levels (30, 100, and 300 mg/kg) with anticonvulsant activity and motor impairment noted 30 min and 4 h (and in some cases 2 h and 6 h) after administration. Results of the Phase I testing are shown in Table VII.

TABLE VII

Anticonvulsant Screening Project (ASP) - Phase I Test Results in Mice (ip)

| Compound | Clog P[a] | Dose, mg/kg | scMet,[b] 30 min | scMet,[b] 4 h | MES,[c] 30 min | MES,[c] 4 h | Tox,[d] 30 min | Tox,[d] 4 h |
|---|---|---|---|---|---|---|---|---|
| 4a | 2.32 | 30 | 0/1 | 0/1 | 0/1 | 0/1 | 0/4 | 0/2 |
| | | 100 | 0/1 | 0/1 | 3/3 | 1/3 | 0/8 | 0/4 |
| | | 300 | 0/1 | 0/1 | 1/1 | 1/1 | 1/4 | 0/2 |
| 4b | 2.85 | 10 | 0/1 | 0/1 | 0/1 | 0/1 | 0/4 | 0/2 |
| | | 30 | 0/1 | 0/1 | 1/3 | 0/3 | 0/8 | 0/4 |
| | | 100 | 0/1 | 0/1 | 1/1 | 0/1 | 0/4 | 0/2 |
| 4c | 3.56 | 30 | 0/1 | 0/1 | 0/1 | 0/4 | 0/4 | 0/2 |
| | | 100[e] | 0/1 | 0/1 | 0/3 | 1/3 | 0/8 | 0/4 |
| | | 300 | 0/1 | 0/1 | 0/1 | 1/1 | 0/4 | 0/2 |
| 4d | 2.46 | 30 | 0/1 | 0/1 | 0/1 | 0/1 | 0/4 | 0/2 |
| | | 100 | 0/1 | 0/1 | 0/3 | 0/3 | 0/8 | 0/4 |
| | | 300 | 0/1 | 0/1 | 0/1 | 0/1 | 0/4 | 0/2 |
| 4e | 3.39 | 30 | 0/1 | 0/1 | 0/1 | 0/1 | 0/4 | 0/2 |
| | | 100 | 0/1 | 0/1 | 0/3 | 2/3 | 0/8 | 0/4 |
| | | 300 | 0/1 | 0/1 | 0/1 | 1/1 | 0/4 | 0/2 |
| 4f | 3.92 | 30 | 0/1 | 0/1 | 0/1 | 0/1 | 0/4 | 0/2 |
| | | 100 | 0/1 | 0/1 | 2/3 | 1/3 | 0/8 | 0/4 |
| | | 300 | 0/1 | 2/5 | 1/1 | 1/1 | 0/4 | 0/2 |
| 4g | 4.63 | 30 | 0/1 | 0/1 | 0/1 | 0/1 | 0/4 | 0/2 |
| | | 100 | 0/1 | 0/1 | 0/3 | 1/3 | 0/8 | 0/4 |
| | | 300 | 0/1 | 0/1 | 0/1 | 1/1 | 0/4 | 0/2 |
| 4h | 2.82 | 30 | 0/1 | 0/1 | 0/1 | 0/1 | 0/4 | 0/2 |
| | | 100[f] | 0/1 | 0/1 | 0/3 | 1/3 | 0/8 | 0/4 |
| | | 300 | 0/1 | nd | 1/1 | 1/1 | 0/3 | 0/1 |
| 4i | 3.35 | 30 | 0/1 | 0/1 | 2/4 | 0/1 | 0/4 | 0/2 |
| | | 100 | 0/1 | 0/1 | 1/3 | 0/3 | 0/8 | 0/4 |
| | | 300 | 0/1 | 0/1 | 1/1 | 1/1 | 0/4 | 0/2 |
| 4j | 3.18 | 10 | 0/1[g] | 0/1[h] | 0/1 | 0/1 | 0/4 | 0/2 |
| | | 30 | 0/1[g] | 0/1 | 1/3 | 0/3 | 0/8 | 0/4 |
| | | 100 | 0/1 | 0/1 | 1/1 | 0/1 | 0/4 | 0/2 |
| 4k | 3.70 | 10 | 0/1 | 0/1 | 0/1 | 0/1 | 0/4 | 0/2 |
| | | 30 | 0/1 | 0/1 | 0/3 | 0/3 | 0/8 | 0/4 |
| | | 100 | 0/1 | 0/1 | 0/1 | 0/1 | 0/4 | 0/2 |
| | | 300 | 0/1 | 0/1 | 3/3 | 3/3 | 0/8 | 0/4 |
| 4l | 4.22 | 3 | nd | nd | 0/4 | nd | nd | nd |
| | | 10 | nd | nd | 0/4 | nd | 0/4 | nd |
| | | 30 | 0/1 | 0/1 | 1/1 | 0/1 | 0/4 | 0/2 |
| | | 100 | 0/1 | 0/1 | 3/3 | 2/3 | 0/8 | 0/4 |
| | | 300 | 1/3 | 0/1 | 1/1 | 1/1 | 0/4 | 0/2 |

[a] ClogP Program; version 1.0.3., BioByte Corp. Clarement, CA 91711.
[b] Subcutaneous pentylenetetrazol test (number of animals protected/number of animals tested).
[c] Maximal electroshock test (number of animals protected/number of animals tested).
[d] Rotorod toxicity (number of animals exhibiting toxicity/number of animals tested).
[e] At 2 h, 1/3 MES animals protected, 1/3 toxic; at 6 h, 0/3 MES animals protected, 0/3 toxic.
[f] At 0.25 h, 2/3 MES animals protected.
[g] Continuous seizure activity.
[h] Death following continuous seizure,
nd = not determined.

To differentiate the results between different rodent species, 4b (X=H), as well as 4a (R=H), 4e (R=Cl), 4f (R=Cl) and 4i (R=CH$_3$) are subsequently evaluated for oral (po) activity in the rat (Phase VIA or VIB). Data are shown in Table VIII.

TABLE VIII

Oral Rat Data

| Compound | Evaluation[a] | Time, h | Dose, mg/kg | MES[b] | Dose, mg/kg | Tox[c] | ED$_{50}$ | TD$_{50}$ |
|---|---|---|---|---|---|---|---|---|
| 1 | Phase VIB | 0.25 | 10 | 3/4 | | nd | 5.8 | >380 |
| | | | (6)[d] | | | | | |
| | | 0.50 | | 4/4 | | nd | | |
| | | | | (3/4)[d] | | | | |
| | | 1.00 | | 4/4 | | nd | | |
| | | | | (2/4)[d] | | | | |
| | | 2.00 | | 4/4 | | nd | | |
| | | | | (1/4)[d] | | | | |
| | | 4.00 | | 3/4 | | nd | | |
| 4a | Phase VIA | 0.25 | 30 | 0/4 | 30 | 0/4 | nd | nd |
| | | 0.50 | | 1/4 | | 0/4 | | |
| | | 1.00 | | 2/4 | | 0/4 | | |
| | | 2.00 | | 1/4 | | 0/4 | | |
| | | 4.00 | | 2/4 | | 0/4 | | |
| 4b | Phase VIB | 0.25 | 30 | 3/4 | 30 | 0/4 | 13.4; 47.2[d] | nd; >500[d] |
| | | 0.50 | | 1/4 | | 1/2 | | |
| | | 1.00 | | 2/4 | | 0/4 | | |
| | | 2.00 | | 0/4 | | 0/4 | | |
| | | 4.00 | | 4/4 | | 0/4 | | |
| 4e | Phase VIA | 0.25 | 30 | 0/4 | 30 | 0/4 | nd | nd |
| | | 0.50 | | 0/4 | | 0/4 | | |
| | | 1.00 | | 3/4 | | 0/4 | | |
| | | 2.00 | | 3/4 | | 0/4 | | |
| | | 4.00 | | 2/4 | | 0/4 | | |
| 4f | Phase VIA | 0.25 | 30 | 0/4 | 30 | 0/4 | nd | nd |
| | | 0.50 | | 1/4 | | 0/4 | | |
| | | 1.00 | | 3/4 | | 0/4 | | |
| | | 2.00 | | 3/4 | | 0/4 | | |
| | | 4.00 | | 3/4 | | 0/4 | | |
| 4i | Phase VIA | 0.25 | 30 | 0/4 | 30 | 0/4 | nd | nd |
| | | 0.50 | | 2/4 | | 0/4 | | |
| | | 1.00 | | 3/4 | | 0/4 | | |
| | | 2.00 | | 1/4 | | 0/4 | | |
| | | 4.00 | | 0/4 | | 0/4 | | |
| 4j | Phase VIA | 0.25 | 30 | 2/4 | 30 | 0/4 | | |
| | | 0.50 | | 3/4 | | 0/4 | | |
| | | 1.00 | | 1/2 | | 0/2 | | |
| 4l | Phase VIA | 0.25 | 30 | 2/4 | 30 | 0/4 | | |
| | | 0.50 | | 2/4 | | 0/4 | | |
| | | 1.00 | | 4/4 | | 0/4 | | |
| | | 2.00 | | 4/4 | | 0/4 | | |
| | | 4.00 | | 4/4 | | 0/4 | | |

[a]For details see Experimental Section.
[b]Maximal electroshock test.
[c]Rotorod toxicity.
[d]Results of a repeat test.
nd = not determined.

Note, that quantitation of the effectiveness of 4b proves difficult. A first measured ED$_{50}$ of 13.9 mg/kg is contrasted with a second measured ED$_{50}$ of 47.2 mg/kg and a TD$_{50}$>500 mg/kg, indicating a protective index (TD$_{50}$/ED$_{50}$) >10.6. This disparity in ED$_{50}$ results is most probably due to solubility difficulties, as these compounds are highly water-insoluble.

A TTE test is performed on the phase I inactive phenothiazine 4d (R=H). Piredda, S. G.; Woodhead, J. H.; Swinyard, E. A. Effect of stimulus intensity on the profile of anticonvulsant activity of phenytoin, ethosuximide and valproate. *J. Pharmacol. Exp. Ther.* 1985, 232, 741–745. The TTE test is a clinically nonselective, electroconvulsive seizure model that identifies compounds that raise seizure threshold as well as those that prevent seizure spread. In addition, this test can identify certain compounds that are inactive by both the MES and the scMet tests. The TTE test is similar to the MES screen but uses a lower level of electrical current. The lower current makes the TTE test more sensitive, but less discriminate than the MES screen. This ability makes the model attractive because it allows for the identification of compounds that may have been omitted by the standard identification screen. If a compound is found to possess significant activity in the TTE test while remaining inactive in the MES rescreen, it becomes a candidate for more advanced testing. These TTE active compounds may represent compounds acting by novel mechanisms.

Twenty mice are pretreated with 100 mg/kg of the test compound. At several time intervals (15 min, 30 min, 1 h, 2 h and 4 h) post treatment with the test compound, four mice at each time point are challenged with 12.5 mA of electrical current for 0.2 sec via corneal electrodes. This stimulation produces a TTE seizure in the animals. For each time interval, results are expressed as a ratio of the number of animals protected over the number of animals tested. Results for 4d are shown in Table IX.

TABLE IX

Threshold Tonic Extension (TTE)[a] test and MES confirmation: Mice ip for 4d.

| Dose, mg/kg | Time, h | TTE Result[b] | MES confirmation[b] |
|---|---|---|---|
| 100 | 0.25 | 1/4 | 0/4 |
|  |  | (2/4)[c] | (1/4)[c] |
|  | 0.50 | 3/4 | 3/4 |
|  |  | (2/4)[c] | (1/4)[c] |
|  | 1.00 | 1/4 | 1/4 |
|  |  | (0/4)[c] | nd |
|  | 2.00 | 3/4 | 0/4 |
|  |  | (0/4)[c] | nd |
|  | 4.00 | 0/4 | nd |
|  |  | (0/4)[c] | nd |
|  | 6.00 | nd | nd |
|  |  | (1/4)[c] | nd |

[a]See reference 12.
[b]Number of animals protected/number of animals tested.
[c]Results of a repeat test.
nd = not determined.

We claim:

1. A method of treating grand mal and partial seizures in a mammal comprising administering to said mammal an effective amount of the phenothiazine of the formula:

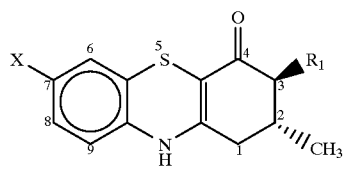

and pharmaceutically acceptable salts thereof, where $R_1$ is H or —COOR, where R is selected from the group consisting of branched or unbranched alkyl groups containing from 1 to 4 carbon atoms, and where X is selected from H, branched or unbranched alkyl groups containing from 1 to 4 carbons, and halogen.

2. The method of claim 1 where X is H, $R_1$ is COOR, and R is methyl.

3. The method of claim 1 where X is H, $R_1$ is COOR, and R is ethyl.

4. The method of claim 1 where X is Cl, $R_1$ is COOR, and R is methyl.

5. The method of claim 1 where X is Cl, $R_1$ is COOR, and R is ethyl.

6. The method of claim 1 where X is methyl, $R_1$ is COOR, and R is ethyl.

7. The method of claim 1 where X is Br, $R_1$ is COOR, and R is methyl.

8. The method of claim 1 where X is Br, $R_1$ is COOR, and R is ethyl.

9. The method of claim 1 where X is Br, $R_1$ is COOR, and R is ter butyl.

* * * * *

UNITED STATES PATENT AND TRADEMARK OFFICE
CERTIFICATE OF CORRECTION

Page 1 of 3

PATENT NO. : 5,994,349
DATED : November 30, 1999
INVENTOR(S) : Kenneth R. Scott, et. al.

It is certified that error appears in the above-indentified patent and that said Letters Patent is hereby corrected as shown below:

In the Title Page:

Column 1, line 9 under "OTHER PUBLICATIONS": Change "4'–, 3' " to –4'–, 3'–.

| Column | Line | |
|---|---|---|
| 1 | 56 | Change "Perzbom" to –Perzborn–. |
| 1 | 61 | Change "drug" to –drugs–. |
| 2 | 15 | After "series" insert –of–. |
| 4 | 37 | Insert: |
| | | –Conditions: |
| | | (a) $Br_2$, KSCN, HOAc, 15°C; (b) NaOH, Δ; (c) DMSO, Δ–. |
| 9 | 30 | After "thereof" insert –.–. |
| 11 | 39 | Change "an" to –are–. |
| 15 | 25 | Change "Larest" to –Largest–. |
| 16 | 63 | Change "literature" to –known–. |

UNITED STATES PATENT AND TRADEMARK OFFICE
CERTIFICATE OF CORRECTION

PATENT NO. : 5,994,349
DATED : November 30, 1999
INVENTOR(S) : Kenneth R. Scott, et. al.

It is certified that error appears in the above-indentified patent and that said Letters Patent is hereby corrected as shown below:

| Column | Line | |
|---|---|---|
| 17 | 8 | Before "into" delete "J". |
| 17 | 11 | Change "tert" to --*tert*--. |
| 17 | 41 | Change "ter" to --*ter*--. |
| 17 | 44 | Change "tert" to --*tert*--. |
| 18 | 46 | Change "ter" to --*ter*--. |
| 18 | 48 | Change "ter" to --*ter*--. |
| 19 | 19 | Change "ter" to --*ter*--. |
| 19 | 21 | Change "ter" to --*ter*--. |
| 19 | 60 | Change "ter" to --*ter*--. |

UNITED STATES PATENT AND TRADEMARK OFFICE
CERTIFICATE OF CORRECTION

PATENT NO. : 5,994,349
DATED : November 30, 1999
INVENTOR(S) : Kenneth R. Scott, et. al.

It is certified that error appears in the above-indentified patent and that said Letters Patent is hereby corrected as shown below:

| Column | Line | |
|---|---|---|
| 20 | 33 | Change "ter" to --*ter*--. |
| 20 | 47 | Change "ter" to --*ter*--. |
| 26 | 31 | Change "ter" to --*ter*--. |

In addition, the text on the following lines should be bold-faced:

Col. 17, lines 14, 36, 41 and 46;

Col. 18, lines 5, 12, 20, 21, 33, 34, 46, 47, 59, and 60;

Col 19, lines 6, 7, 19, 20, 33, 34, 46, 47, 59 and 60;

Col. 20, lines 5, 6, 18, 19, 32, 33, 45 and 46.

Signed and Sealed this

Tenth Day of April, 2001

NICHOLAS P. GODICI

Attest:

Attesting Officer

Acting Director of the United States Patent and Trademark Office